United States Patent
Baron et al.

(10) Patent No.: US 8,175,822 B2
(45) Date of Patent: May 8, 2012

(54) METHOD FOR MEASURING THE PRESSURE AND/OR MOLAR MASS OF A GAS IN A HOUSING, AND CORRESPONDING MEASUREMENT ASSEMBLY

(75) Inventors: Daniel Baron, Manosque (FR); Jean-Yves Ferrandis, Saint Gely Dufesc (FR); Gérard Leveque, Montpellier (FR); Didier Laux, Caveirac (FR); Eric Rosenkrantz, Prades le Lez (FR)

(73) Assignees: Electricite de France, Paris (FR); Centre National de la Recherche, Paris (FR); Universite Montpellier 2 Sciences et Techniques, Montpellier (FR)

( * ) Notice: Subject to any disclaimer, the term of this patent is extended or adjusted under 35 U.S.C. 154(b) by 368 days.

(21) Appl. No.: 12/524,356

(22) PCT Filed: Jan. 25, 2008

(86) PCT No.: PCT/EP2008/050864
§ 371 (c)(1),
(2), (4) Date: Jul. 23, 2009

(87) PCT Pub. No.: WO2008/095793
PCT Pub. Date: Aug. 14, 2008

(65) Prior Publication Data
US 2010/0010750 A1    Jan. 14, 2010

(30) Foreign Application Priority Data
Jan. 26, 2007 (FR) .................................. 07 52922

(51) Int. Cl.
*G01N 29/00* (2006.01)
*G06F 19/00* (2011.01)

(52) U.S. Cl. ............................................. 702/54

(58) Field of Classification Search ............ 702/54
See application file for complete search history.

(56) References Cited

U.S. PATENT DOCUMENTS

| | | | | |
|---|---|---|---|---|
| 3,557,605 A | * | 1/1971 | Lanneau et al. | 73/24.01 |
| 3,769,839 A | * | 11/1973 | Innes | 374/118 |
| 4,869,097 A | * | 9/1989 | Tittmann et al. | 73/52 |
| 5,753,827 A | * | 5/1998 | Cage | 73/861.356 |

(Continued)

FOREIGN PATENT DOCUMENTS

FR    2 739 925 A1    4/1997

(Continued)

*Primary Examiner* — Cindy H Khuu
(74) *Attorney, Agent, or Firm* — Blakely, Sokoloff, Taylor & Zafman

(57) ABSTRACT

The invention relates to a method for measuring the pressure and/or molar mass of a gas in a housing, the measure being carried out via an acoustic sensor, said acoustic sensor at least one transducer (5), an electric system (8) connected to the transducer (5) and a coupling layer (6) for coupling the transducer (5) to the housing (1), said method comprising the following steps: generating using the transducer (5) an excitation acoustic signal that vibrates the housing (1) and the gas (2) in a wide frequency band; detecting with the transducer (5) a response acoustic signal characteristic of the vibrations of the housing and the gas; analysing the response electric signals from the transducer (5) using the system (8); and deriving, essentially based on the gas (2) resonance frequencies, the speed of the acoustic waves in the gas, the molar mass of the gas and the pressure thereof. The invention also relates to an assembly for implementing the method.

12 Claims, 3 Drawing Sheets

U.S. PATENT DOCUMENTS

| | | | |
|---|---|---|---|
| 6,279,379 B1 * | 8/2001 | Logue et al. | 73/24.01 |
| 6,912,918 B1 * | 7/2005 | Lynnworth et al. | 73/861.26 |
| 2003/0164038 A1 * | 9/2003 | Han et al. | 73/152.58 |
| 2005/0268703 A1 | 12/2005 | Funck et al. | |
| 2008/0134756 A1 * | 6/2008 | Riddle | 73/24.02 |

FOREIGN PATENT DOCUMENTS

WO     WO 00/73781 A1    12/2000

\* cited by examiner

Example of calibration

METHOD FOR MEASURING THE PRESSURE AND/OR MOLAR MASS OF A GAS IN A HOUSING, AND CORRESPONDING MEASUREMENT ASSEMBLY

This is a non-provisional application claiming the benefit of International application number PCT/EP2008/050864 filed Jan. 25, 2008.

GENERAL TECHNICAL FIELD

The present invention concerns a method according to the preamble of claim 1.

It also concerns an assembly according to the preamble of claim 7.

BACKGROUND OF THE INVENTION

One would like to be able to access the value of the pressure in a cylindrical housing filled with a gaseous mixture, for example in order to measure the internal pressure of a fuel rod of a nuclear power plant reactor.

One would also like to determine the molar mass of the aforementioned gaseous mixture.

In order to access this type of information, in general it is necessary to use destructive methods, such as piercing of the housing.

One can also use methods based on the presence of a radioactive tracer gas (such as Krypton 85, for example). However, these methods are not applicable when one wishes to measure the pressure in a tube which is part of a bundle of tubes containing the same radioactive tracer.

We know from FR 2 739 925 an acoustic sensor comprising:
- at least one transducer generating an acoustic wave and/or receiving an acoustic wave in return;
- a glass bar to transmit the acoustic waves, and
- a liquid coupling layer of the sensor with the rod, the layer having a defined thickness $\lambda/4$, $\lambda$ corresponding to twice the acoustic thickness of the wall of the rod.

The sensor makes it possible to derive the pressure of the gas in the void volume of the fuel rod, thanks to the amplitude of the waves reflected in the transducer.

The sensor does, however, have drawbacks.

First, it only allows measurement of the pressure of the gas, and not of its molar mass.

Furthermore, the liquid coupling layer in $\lambda/4$ allows good transmission of the acoustic waves in the rod, but only in a small frequency interval around the resonance frequency of a stack formed by the sensor and the rod.

Moreover, the amplitude of the resonances of the gas is of course sensitive to the pressure, but also to disturbances or poorly known sizes, such as the absorption of the gas or the flaws of the rod walls. Thus, even after calibration, the precision of the measurements remains low.

Lastly, the measuring method does not make it possible to work with rods containing an object causing dispersion of the waves, such as a spring.

Furthermore, WO 00/73781 discloses a housing characterization technique by a remote sensor (and not in contact, as in FR 2 739 925) working through vibrations of the housing (and not of the gas, as in FR 2 739 925) and furthermore in much smaller frequency fields than those disclosed by FR 2 739 925.

BRIEF DESCRIPTION OF THE INVENTION

The invention proposes to offset at least one of the aforementioned drawbacks.

To this end, proposed according to the invention is a method according to claim 1.

The invention is advantageously completed by the characteristics covered in dependent claims 2 to 6.

The invention also concerns an assembly for implementing the method.

In particular, proposed according to the invention is an assembly according to claim 7.

The invention is advantageously completed by the characteristics covered in dependent claims 8 to 12.

The invention presents a number of advantages.

The new "sensor-housing" coupling is designed to allow transmission in a much broader spectral band than that of the prior art. The acoustic stack formed by the housing, the coupling layer and the transducer can vibrate in a wide frequency band. Preferably, the width of the band must reach 1 MHz for the current housing walls in zirconium alloy vibrating in the vicinity of 4 MHz, or 25% in relative value.

The broadband sensor makes it possible to excite many resonances of the gas. Exciting a number of resonances of the gas makes it possible, through the average effect in suitable processing (in particular using the integral J of the spectral response of the gas), to free oneself from the absorption of the gas, and in large part from the imperfections of the housing.

The sensor makes it possible to noticeably increase precision on pressure measurements.

The sensor and the associated measuring method allow measuring on housings containing a spring, the effect of this spring then being simply considered an additional attenuation.

Moreover, the broadband measuring method makes it possible to increase the precision of the measurement of the celerity of the acoustic waves, and also that of the molar mass of the gaseous mixture.

The sensor and the measuring method have a number of applications.

They allow tests on nuclear fuel rods, in service and in storage.

They allow nondestructive measurements of the pressure and molar mass of gas in the nuclear fuel rods, in particular containing primarily a gaseous mixture of Helium, Xenon and Krypton. The measurement is done on the top portion of the rod, in the expansion chamber of the fuel column, at the maintenance spring.

The measuring method can be implemented in pool at the intercycles, during shutdowns. The sensor then makes it possible to:
- detect one or several non-sealing fuel rods in an assembly comprising a plurality of rods;
- help in the refueling decision for the power plant assembly;
- help in decisions before reversible storage;
- increment the statistical support base for the digital simulation.

The implementation for nondestructive hot cell examinations (cells shielded in order to operate on active materials), with the same objectives, is also possible.

BRIEF DESCRIPTION OF THE DRAWINGS

Other characteristics, objects and advantages of the invention will emerge from the following description, which is purely illustrative and non-limiting, and which must be read in regard to the appended drawings in which.

In all of the figures, the similar elements bear identical numerical references.

DETAILED DESCRIPTION OF THE INVENTION

Figures 1A, 1B:
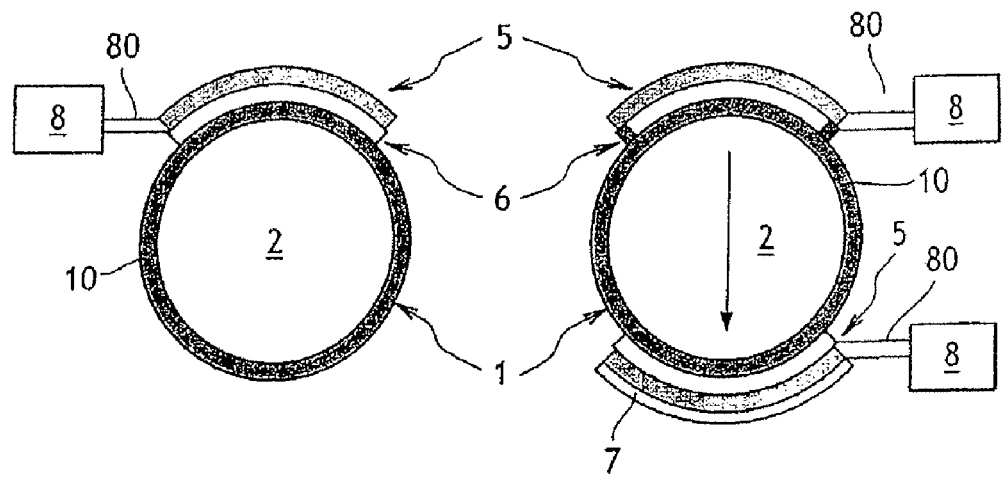
FIGS. 1A and 1B diagrammatically illustrate two embodiments, on a housing, of examples of sensors according to the invention, each sensor and the housing then forming an acoustic stack.

In FIGS. 1A and 1B we have diagrammatically shown a housing 1 containing a gas 2.

The housing 1 is for example a fuel rod and the gas 2 is for example helium or a mixture of gases.

The housing 1 supports an acoustic sensor.

The sensor coupled to the housing therefore forms an assembly formed on one hand by the sensor and on the other hand by the housing.

The acoustic sensor allows the measurement of at least one physical parameter of the gas 2, such as the pressure of the gas in the housing and/or its molar mass, for example.

The acoustic sensor comprises:

at least one transducer 5 in order to
- on one hand, generate an acoustic signal vibrating the housing and the gas, and
- on the other hand, detect an acoustic response signal characteristic of the vibrations of the gas and the housing;

a coupling layer 6 between the transducer 5 and the housing 1;

an electrical system 8 which is connected to the transducer 5 and which allows:
- excitation of said transducer 5, and
- analysis of the response signals.

In general, the housing has a cylindrical rotary shape—this is the case in particular for the fuel rods, for example.

One understands, however, that the housing can have any cylindrical shape whatsoever, such as with flat parallel faces, for instance.

In the case of a cylindrical rotary shape, preferably, all of the elements of the sensor are concentric.

The transducer 5 can comprise a back 7. The back 7, which has reflection or absorption capacities for the acoustic signals, has an influence on the acoustic properties of the sensor. The use of resonating backs must not disrupt the spectral usage band of the sensor.

The system 8 transmits electric signals to the transducer 5. The transducer 5 converts the electric signals into acoustic signals, and vice versa. To this end, the transducer 5 is traditionally of the piezoelectric type (for example a PZT material—Lead Zirconium Titanium oxide).

The coupling layer 6 can assume several forms, such as a liquid or a solid. It is contained in the volume defined by the inner face of the transducer 5, the outer face of the housing 1 and wedges 9 inserted between these two faces. The wedges 9 are optional in the case of a solid layer 6.

In the case of a solid layer 6, one must ensure proper transmission of the acoustic waves to the interfaces, either by splicing or by a very thin layer of liquid couplers. If the effect of these thin layers is not negligible, they should be included in the transit time recommended in table 1 below.

When the sensor is placed on the housing 1, one is then in the presence of an acoustic stack formed by the wall 10 of the housing 1, the coupling layer 6 and the transducer 5. The wall 10 of the housing 1 and the transducer 5 have a strong acoustic impedance, while the gas 2 and the coupling layer 6 have a low acoustic impedance.

According to the invention, the various thicknesses of piezoelectric materials 5 and the coupling layer 6 are granted at the free resonance frequency of the wall 10.

This agreement is defined according to the travel time of the layer 6 by the acoustic waves.

$T_{10}$ is the travel time from the wall 10 of the housing 1 by the acoustic waves, $T_{10} = e_{housing}/c_{housing}$, with $e_{housing}$ and $c_{housing}$ being the thickness of the wall and the celerity of the acoustic waves in the wall, respectively. The first free resonance period of this wall is then $2T_{10}$. We call this resonance the $\lambda/2$ mode.

$T_5$ is the travel time from the transducer 5 by the acoustic waves. The transducer 5 must vibrate in the same mode $\lambda/2$ at the same frequency as the wall 10, so the thickness of the transducer 5 is such that $T_5$ equals $T_{10}$.

The acoustic impedance of the transducer is in the vicinity of $30 \cdot 10^6$ PA·s·m$^{-3}$ for PZT.

The thickness of the coupling layer 6 is also determined from $T_{10}$. Several cases can be considered.

TABLE 1

| Acoustic impedance of the coupling layer in $10^6$ SI (Pa · s · m$^{-3}$) | Transit time $T_6 = [n - (½)]T_{10}$ | Transit time $T_6 = n\, T_{10}$ |
| --- | --- | --- |
| 0.5 < Z < 3 | narrow band | broad band |
| 3 < Z < 15 | broad band | | n is a whole number, preferably equal to 1

The case of a transit time $T_6$ equal to $T_{10}/2$ (thickness called $\lambda/4$) in water (Z=1.5 $10^6$ SI) corresponds to the sensor disclosed in FR 2 739 925. This is a "narrow band" system.

The precision achieved on the transit time must be ±20% on a standard assembly; however, the closer the transit time comes to the conditions of the table, the greater the reproducibility of the measurements, because one is then on one extremum of the response of the sensor.

For a coupling layer having an acoustic impedance between 0.5 $10^6$ and 3 $10^6$ SI (case of liquids for example), these precisions give an acoustic thickness between 0.4λ and 0.6λ, where λ is the wavelength, in the coupling layer, at the frequency $f_0$ of free vibration of a wall 10 of the housing 1 with $f_0 = c_{housing}/(2\, e_{housing})$.

Also, for a coupling layer having an acoustic impedance comprised between $3.10^6$ and $15.10^6$ SI (case of solids for example) an acoustic thickness of the layer is obtained, comprised between 0.2λ and 0.3λ wherein λ is the wavelength in the coupling layer at the frequency $f_0$ of free vibration of a wall 10 of the housing 1.

Figure 2:
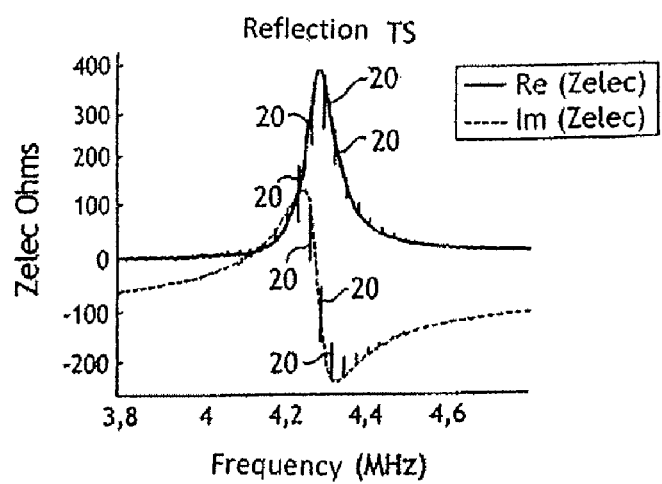
FIG. 2 diagrammatically illustrates the electric impedance of the aforementioned acoustic stack according to the frequency.

FIG. 2 shows the impedance of a sensor working in reflection (case of assembly of FIG. 1A). A band with a width of 0.3 MHz for a central frequency—i.e. a resonance frequency of the free wall 10—of 4 MHz corresponds to a fairly unsatisfactory sensor. Preferably, the bandwidth is in the vicinity of 20% of the central resonance frequency, or even 25%.

The two cases marked "broad band" correspond to the broadband sensor according to the invention. The acoustic sensor is designed to have a sensitivity in a broad spectral band rather than a high sensitivity at only one frequency.

More generally, we call "broad band" a frequency bandwidth which is such that at least two, preferably in the vicinity of ten, resonances of the gas are generated.

In other words, the acoustic sensor is characterized in that its frequency band for transmission of acoustic signals has a width L such that:

$$L \geq \frac{c}{D}$$

where c is the celerity of the acoustic waves in the gas of the housing, and

D is the inner dimension of the housing, the transmission frequency band being centered around $f_0$, where $f_0$ is the free vibration frequency of a wall of the housing to which the sensor is coupled upon a measurement $f_0$.

The electric part of the sensor will now quickly be described. The transducer 5 is for example a PZT (Lead Zirconium Titanium oxide) tile. The transducer 5 can also be a piezoelectric polymer composite. These transducers can broaden the spectral usage band of the sensor, by decreasing the quality factor of the sensor.

The transducer 5 is connected to the system 8 by conductive wires 80.

The system 8 comprises on one hand, a voltage generator, and on the other hand, means for measuring the voltage supplied by the sensor according to the frequency V(f), or its temporal response V(t) to a voltage pulse. These measurements make it possible to determine the pressure and molar mass of the gas in the housing, as described below in reference to FIG. 4.

Figure 3A:
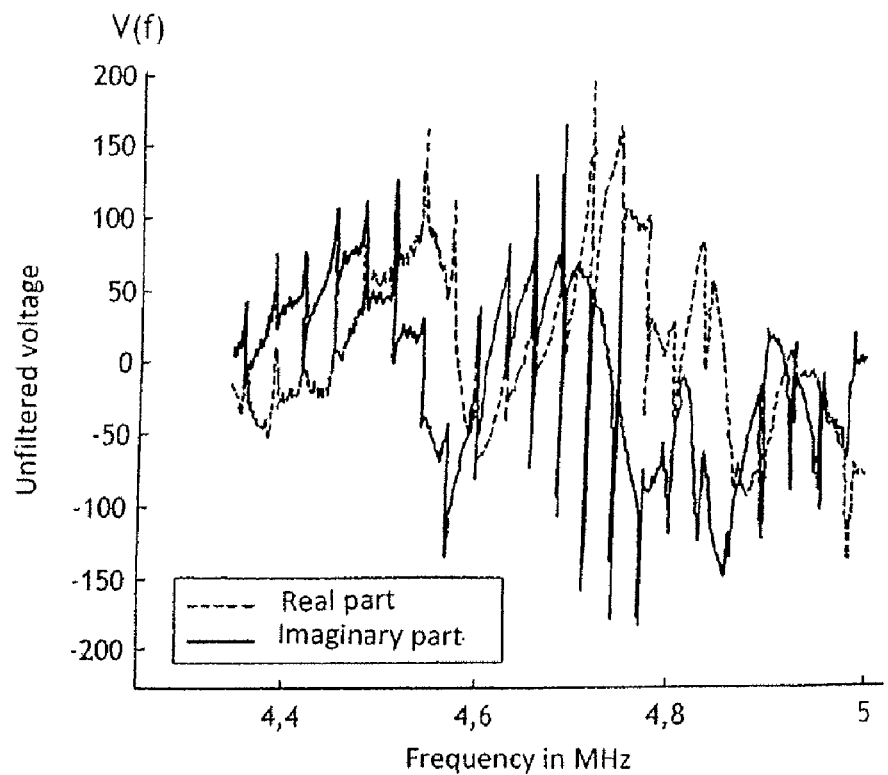
FIG. 3A illustrates a curve of the Real and Imaginary parts of the unfiltered voltage according to the frequency.

A first step 41 of the method consists for example of exciting the transducer 5 using the system 8 with a sinusoidal voltage U with adjustable frequency in the useful field. From this, one derives a frequency response spectrum with voltage V(f) of FIG. 3A.

Another possibility for the first step (step 42) consists of exciting the transducer 5 by a series of pulses. One obtains a voltage V(t). A Fourier transformation of the electric signals coming from the transducer 5 is necessary to derive a frequency response spectrum V(f) of the system as previously.

The complex spectrum V(f) (step 43) constitutes the starting point for processing of the signal.

Figure 4:
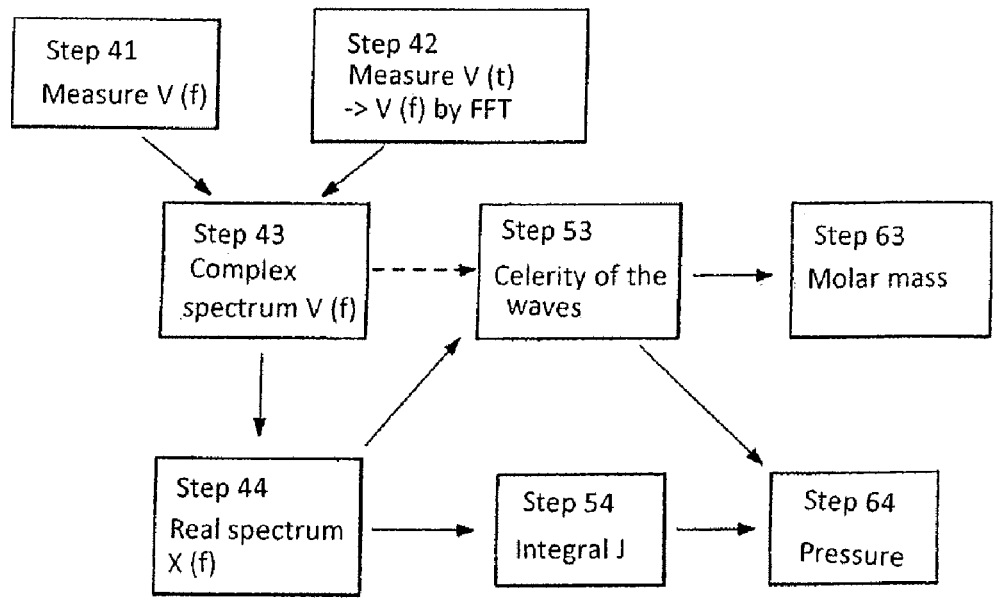
FIG. 4 diagrammatically illustrates the main steps of an example of an embodiment of the sensor.

The processing of the spectrum resulting from the two steps above is then common, as shown by FIG. 4.

The global response of the sensor is made up of the resonances of the gas 2 and the resonances of the acoustic sensor coupled to the housing 1.

However, the resonances of the gas 2, being due to the radial stationary waves in the housing 1, are periodic according to the frequency. They are therefore easily distinguishable and can be separated from other resonances.

The resonances due to the gas 2 are those corresponding to the peaks 20 on the curves of FIG. 2.

Figure 3B:
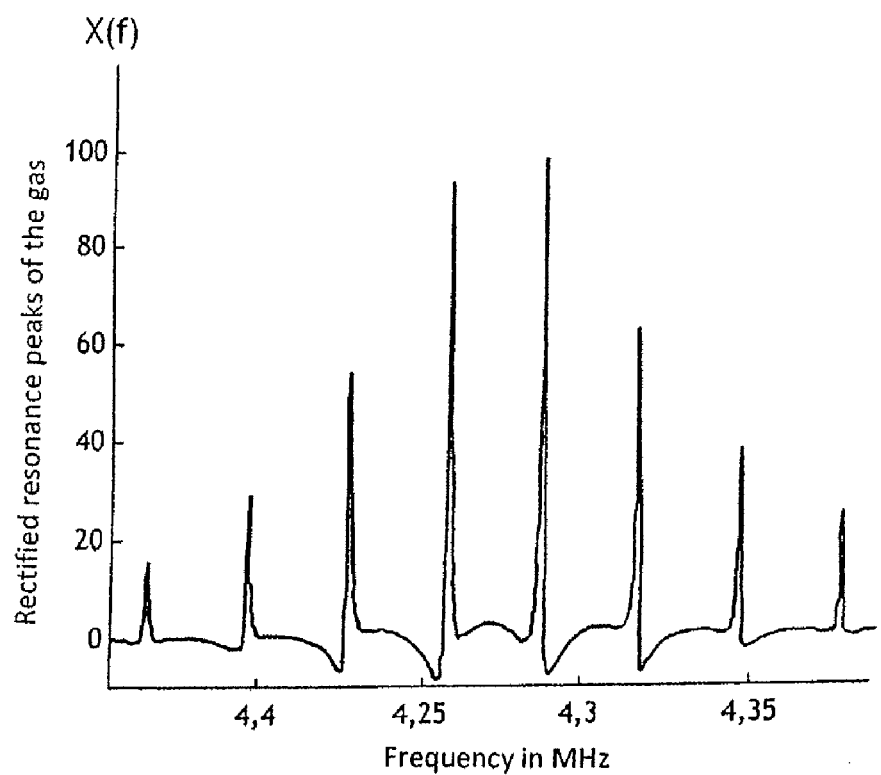
FIG. 3B illustrates an example of response of the gas resonances which appear rectified, the response of the transducer, the coupling layer and the housing 1 being removed.

During step 44, one performs a mathematical transformation on the complex frequency spectrum of FIG. 2 in order to obtain a real curve X(f) in which the resonances of the gas appear alone and rectified, the resonances of the transducer 5, the layer 6 and the housing 1 being removed (as in FIG. 3B). This digital processing of the spectral response of the sensor is necessary in order to correct the variable phases of the resonances of the gas. One possible processing consists of subtracting the slowly variable portions from V(f) (by clipping in the temporal space, for example), then taking the module of the signal.

Step 53 consists of measuring the gap $\Delta f$ between at least two resonance frequencies of the gas. One then derives the celerity c of the acoustic waves in the gas from said gap $\Delta f$. Two cases can occur, depending on whether the measurement is done with one or two sensors.

1/In FIG. 1A, the transducer 5 is unique and works "in reflection". It generates the acoustic waves toward the housing and receives the acoustic waves coming from the housing 1. In this case, the celerity c of the acoustic waves in the gas is derived by:

$$c = 2D\Delta f$$

where D is the inner diameter of the housing in the case of a cylindrical rotary housing. In the case of a housing with parallel flat faces, one understands that D refers to the inner dimension which is crossed by the waves between the two walls of the housing.

2/In FIG. 1B, mounting is anticipated, around the housing, of two sensors positioned symmetrically on either side of the housing 1. A transducer 5 generates an acoustic excitation signal which vibrates the housing and the gas, and another transducer 5 detects the response vibration. The interest of this assembly is to separate the excitation signal and the response signal. In this case, the celerity c of the acoustic waves in the gas is derived by:

$$c = D\Delta f$$

In both cases, better precision is achieved if one measures the gap $\Delta f$ between several resonances (average of several gaps between the peaks 20 of FIG. 2, for example), or if one determines the gap $\Delta f$ through mathematical processing of the positions of the resonances (one possible processing is the transformed Fourier type, for example), hence the need to have a system able to excite the gas in a broad spectral band.

Step 53 can be done on the complex spectrum V(f) resulting from step 43, but preferably on the real response X(f) resulting from step 44, for which periodicity search methods can be used.

In step 63, one can calculate the molar mass M of the gas from the celerity c derived from step 53:

$$M = \frac{\gamma RT}{c^2}$$

where R is the constant of the ideal gases, $\gamma$ is the ratio of the specific heats for the ideal gases, and T is the temperature.

The relation above is valid for the ideal gases. In the case of a mixture of gases, corrections resulting from the equation of real gases can be introduced.

In the case of a binary mixture of monoatomic gases such as a Helium-Xenon mixture, measuring the molar mass allows an immediate derivation of the mass composition x of the mixture, because:

$$M = xM_{Xe} + (1-x)M_{He}$$

Where $M_{Xe}$ and $M_{He}$ are the atomic masses of xenon and helium.

Step 54 allows the measurement of the pressure of the gas. The measuring principle is as follows.

The amplitude of the resonances of the gas observed on the response X(f) of FIG. 3B is proportionate to the acoustic impedance of the gas in the housing 1 and makes it possible to derive the pressure using the steps explained below.

The acoustic impedance $Z_{gaz}(f)$ of the gas, for example in a rigid cavity with flat parallel faces, is written:

$$Z_{gaz}(f) = \frac{\rho c}{i \tan(kD)}$$

where
 ρ is the density of the gas,
 c is the celerity of the gas,
 $i^2 = -1$, $$k = \frac{2\pi f}{c} - i\alpha,$$

α is the absorption coefficient of the gas, and
D is the inner dimension of the housing.

The integral I of the acoustic impedance of the gas, for a resonance, has the property of being independent of the absorption of the gas. It is in fact expressed by:

$$I = \int Z_{gaz} df = \frac{\rho c^2}{2D}$$

Of course, the amplitude of the resonances of the gas observed over the curve X(f) is not a measure of the impedance of the gas, but is modulated by the relative sensitivity S(f) of the sensor, function which depends on the frequency. One therefore cannot derive the pressure from a measurement over only one resonance of the gas.

The relative sensitivity S(f) of the sensor being a stable characteristic of the sensor, the sum of the integrals I for all of the resonances present in the observation window of the sensor, size called STG (Total Sensitivity to the Gas), is a size which depends solely on the gas.

$$STG = I \sum_n S_n$$

where $S_n$ is the relative sensitivity of the sensor for the nth resonance frequency of the gas.

This size does not need to be precisely known, as the sensor requires calibration. In the ideal case where the sensor is sensitive in a window of width F, in which the sensitivity would be constant equal to S, then $$STG = mIS$$

where m is the number of resonances present in the window.
As the resonances are distant from $$\Delta f = \frac{c}{2D},$$

then $$m = \frac{F}{\Delta f} = \frac{2DF}{c}$$

For the ideal gases:

$$PV = nRT,$$

$$\rho = \frac{nM}{V}$$

from which $$\rho c = \gamma \frac{P}{c}$$

The total sensitivity to the gas becomes:

$$STG = FS\rho c = FS\gamma \frac{P}{c}$$

where γ is the ratio of the specific heats for the ideal gases.

Ideally, the STG measurement is proportionate to the pressure of the gas. The need to have a broadband sensor is necessary in order to have many resonances in the integration window and stabilize the integral.

In step 54, by similarity with the ideal case above, one calculates the integral J of the experimental frequency response X(f) in the field F of sensitivity of the sensor:

$$J_{theorique} = \int_F X(f) \cos(2\pi fnT) df = \chi \frac{P}{c}$$

With T, fundamental resonance period of the gas and n, order of the chosen harmonic.

The case n=1 is the most favorable.

This integral is proportional P/c and allows measurement of the pressure P if one knows the constant !.

However, the constant χ is characteristic of a sensor. It unfortunately cannot be derived with sufficient precision from the dimensions and properties of the materials of the sensor.

Figure 5:
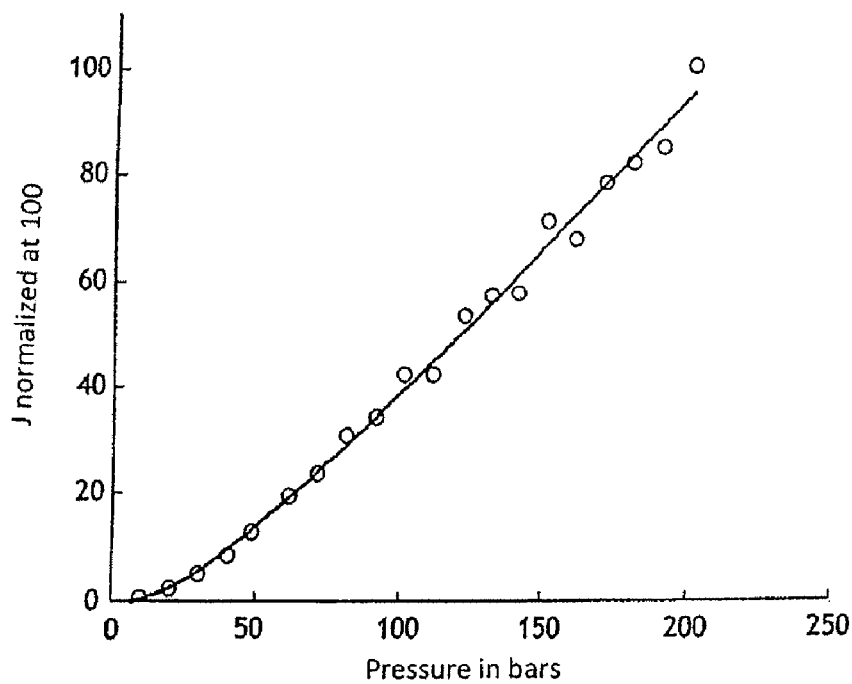
FIG. 5 is an example of a calibration curve of the sensor.

Moreover, a theoretical and experimental study of the integral J shows that the preceding reasoning is only a first approximation. The integral J in fact depends slightly on the absorption of the gas, which makes the function J(P) nonlinear (see FIG. 5). The function J(P) is quasi-linear for high pressures (around 100 bars); however, the response of the system disappears for low pressures (<20 bars) because the gas is very absorbent.

In conclusion, the function J(P,c) can only be obtained through prior calibration of the sensor with a known gas, according to the pressure P and the nature of the gas (in order to vary c). For a measurement on an unknown gas, one first derives c in step 53, then one derives P in step 64 from reading calibration curves obtained with the sensor used, for the celerity c.

The invention claimed is:

1. A method for measuring at least one of a pressure and a molar mass on a housing filled with a gas, the measuring being carried out via an acoustic sensor, the acoustic sensor comprising at least one transducer, an electric system connected to the transducer and a coupling layer for coupling the transducer to the housing, the method including the steps of:
 generating, using the transducer, an excitation acoustic signal that vibrates the housing and the gas in a wide frequency band;

detecting, with the transducer, a response acoustic signal characteristic of the vibrations of the housing and the gas;

converting, with the transducer, the response acoustic signal into the response electric signals;

analyzing the response electric signals from the transducer using the electric system;

measuring an amplitudes of the response electric signals resulting from the transducer in order to determine all of the resonance frequencies of the gas, the transducer, the layer and the housing;

extracting at least two resonance frequencies of the gas from all of the resonance frequencies;

measuring a gap between the at least two resonance frequencies of the gas;

deriving, based on the gap of said gas, a celerity c of a acoustic waves in the gas;

calculating the molar mass M of the gas by:

$$M = \frac{\gamma RT}{c^2}$$

where R is a constant of an ideal gas, T is a temperature and γ is a ratio of a specific heat for the ideal gas; and calculating the pressure P of the gas by using the celerity c of the acoustic waves in the gas and an integral J of a real response acoustic signal X(f) of the gas in the housing, where X(f) is a real curve J(P,c) in which the resonance frequencies of the gas appear alone and rectified, and the resonance frequencies of the transducer, the layer and the housing being removed.

2. The method according to claim 1, comprising, in the case where the system excites the transducer through a series of temporal pulses, a conversion step, in the space of the frequencies, by Fourier transformation, of the temporal electric signals from the transducer.

3. The method according to claim 1, comprising a step for use of the property according to which the resonance frequencies of the gas in the housing are periodic, in order to extract the resonance frequencies of the gas in the enclosure.

4. The method according to claim 1, in which
if the sensor comprises a single transducer working in reflection, the celerity c of the acoustic waves in the gas is derived by:

$c=2D\Delta f$ where D is the inner dimension of the housing and where Δf is the gap between two resonance frequencies of the gas, and;

if the sensor comprises two transducers working in transmission, one transducer generating an acoustic signal spreading toward the housing and another transducer detecting a response acoustic signal, the celerity c of the acoustic waves in the gas is derived by:

$c=D\Delta f.$

5. The method according to claim 1, in which the integral J of the response of the sensor is calculated by:

$J=\int_F X(f)\cos(2\pi fnT)df$ with T, fundamental resonance period of the gas and n, order of the chosen harmonic, where F is the sensitivity frequency width of the sensor and X(f) is a real curve in which the resonances of the gas appear alone and rectified, the resonances of the transducer, the layer and the housing being removed, J being significant of the pressure, pressure which can be derived by calibration.

6. The method according to claim 1, in which the width of the frequency band is such that at least two, preferably in the vicinity of ten, resonances of the gas are generated.

7. An assembly made up of an acoustic sensor and a housing containing a gas, the assembly allowing implementation of a method according to claim 1 when the acoustic sensor is coupled to the housing, the acoustic sensor comprising:
at least one transducer to:
generate an acoustic signal in a wide frequency band which vibrates the housing and the gas, and
detect a response acoustic signal characteristic of the vibrations of the housing and the gas;
a coupling layer to couple the transducer to the housing; and
an electric system connected to the transducer which allows
the excitation of said transducer, and
the analysis of the response acoustic signal;
wherein the wide frequency band for transmission of the acoustic signal having a width L such that:

$$L \geq \frac{c}{D}$$

where c is the celerity of the acoustic waves in the gas of the housing, and
D is an inner dimension of the housing, and
the wide frequency band being centered around $f_0$, where $f_0$ is a free vibration frequency of a wall of the housing to which the acoustic sensor is coupled during the measuring.

8. The sensor according to claim 7, in which the coupling layer has:
an acoustic impedance between $0.5 \cdot 10^6$ and $3 \cdot 10^6$ SI, and
an acoustic thickness between 0.4λ and 0.6λ, where λ is the wavelength, in the coupling layer, at the free vibration frequency of a wall of the housing.

9. The sensor according to claim 7, in which the coupling layer has:
an acoustic impedance between $3 \cdot 10^6$ and $15 \cdot 10^6$ SI, and
an acoustic thickness between 0.2λ and 0.3λ, where λ is the wavelength, in the coupling layer, at the free vibration frequency of a wall of the housing.

10. The sensor according to claim 7, in which the transducer is of the piezoelectric type, with an acoustic thickness equal to 0.5λ, where λ is the wavelength in the transducer, at the free vibration frequency of a wall of the housing.

11. The sensor according to claim 10, in which the transducer has a concentric shape with the housing.

12. The sensor according to claim 7, also comprising a support back of the transducer, the back having reflection or absorption capacities of the acoustic signal.

* * * * *